US006869989B2

(12) United States Patent
Khan et al.

(10) Patent No.: US 6,869,989 B2
(45) Date of Patent: Mar. 22, 2005

(54) METHOD OF MODIFYING COMPONENTS PRESENT IN CASHEW NUT SHELL LIQUID

(75) Inventors: Mohammed Lokman Khan, Bangor (GB); Jeremy Tomkinson, Siloh (GB); Richard James Salisbury, Anglesey (GB)

(73) Assignee: Cambridge Biopolymers Limited, Cambridgeshire (GB)

( * ) Notice: Subject to any disclaimer, the term of this patent is extended or adjusted under 35 U.S.C. 154(b) by 132 days.

(21) Appl. No.: 09/866,451

(22) Filed: May 25, 2001

(65) Prior Publication Data

US 2002/0004576 A1 Jan. 10, 2002

Related U.S. Application Data

(63) Continuation of application No. PCT/GB99/03913, filed on Nov. 25, 1999.

(30) Foreign Application Priority Data

Nov. 25, 1998 (GB) .............................................. 9825679
Jun. 18, 1999 (GB) .............................................. 9914108

(51) Int. Cl.$^7$ ............................. C08J 5/10; C08L 99/00
(52) U.S. Cl. .............................. 524/14; 524/9; 524/13; 524/15; 524/16
(58) Field of Search ................................ 524/9, 13, 14, 524/15, 16

(56) References Cited

FOREIGN PATENT DOCUMENTS

| FR | 2 617 845 A | 1/1989 |
| JP | 45 026750 | 6/1970 |
| JP | 59 076580 A | 5/1984 |
| WO | 00/78699 | * 12/2000 |

OTHER PUBLICATIONS

A. Yasuhara et al., "Analysis of aldehydes and ketones in the headspace of heated pork fat," *Journal of Food Science*, 54:1471–1472, 1484 (1989).
H. Itokawa et al., "Antitumor principles from Ginkgo bilboa L," *Chemical and Pharmaceutical Bulletin*, 35:3016–3020 (1987).
E. H. Pryde et al., "Ozonization of soybean oil. The preparation and some properties of aldehyde oils," *J. Amer. Oil Chemists ' Soc.*, 38:375–379 (1961).
Derwent Abstract XP00213196, filed May 1, 1984, (JP 59 076580 A).
Derwent Abstract XP00213197, filed Jun. 29, 1970, (JP 45 026750).

* cited by examiner

*Primary Examiner*—Rabon Sergent
*Assistant Examiner*—U. K. Rajguru
(74) *Attorney, Agent, or Firm*—Heslin Rothenberg Farley & Mesiti P.C.

(57) ABSTRACT

Disclosed is a process for modifying cashew nut shell liquid (CNSL) which involves the steps of subjecting the CNSL to ozonolysis to form ozonolysis reaction products, followed by reduction of the ozonolysis reaction products to give a mixture of phenolic components and aldehydes. In a preferred embodiment, the process involves reacting CNSL with ozone to form a mixture containing ozonolysis reaction products, and then treating the mixture under reducing conditions to form a further mixture containing phenolic components with an eight carbon chain having a terminal —CHO group and alkyl components of varying lengths with either one or two terminal —CHO groups. The resulting CNSL aldehydes may be used to form adhesives for use in the manufacture of composites such as wood particle board.

14 Claims, No Drawings

US 6,869,989 B2

METHOD OF MODIFYING COMPONENTS PRESENT IN CASHEW NUT SHELL LIQUID

CROSS REFERENCE TO RELATED APPLICATIONS

This application is a continuation of co-pending International Patent Application Number PCT/GB99/03913, filed Nov. 25, 1999, and claims priority from GB Patent Application Numbers 9914108.7, filed Jun. 18, 1999 and 9825679.5, filed Nov. 25, 1998. The entire disclosures of the prior applications are incorporated herein by reference.

FIELD OF THE INVENTION

This invention relates to a method of modifying components present in cashew nut shell liquid (CNSL), so as to improve its utilisation as a raw material for the formation of polymeric materials, particularly to be used as binders in the formation of composite products.

BACKGROUND OF THE INVENTION

CNSL is extracted from the outer shell of the cashew nut obtained from the cashew nut tree, *Anacardium Occidentale L.* CNSL is a mixture of phenolic compounds and the compounds which can be present in varying proportions include anacardic acid, cardanol, cardol, and 2-methyl cardol. Each of these compounds has a 15 carbon (pentadecyl) side chain, and each compound can occur with this side chain fully saturated, or in one of three forms of unsaturation; monoene, unsaturated at the 8' position, diene, unsaturated at the 8' and 11' positions, and triene, unsaturated at the 8', 11', and 14' positions. CNSL is available as natural CNSL and also as so-called "technical CNSL". The ratio of the components present in the two forms differs because there is a heating step during the formation of technical CNSL which causes the decarboxylation of some or all of the anarcardic acid which increases the proportion of cardanol. This heating step also leads to the formation of some polymerised material.

The presence of phenol groups means that CNSL can be used to form adhesives analogous to phenol formaldehyde adhesives by reacting with aldehydes in the presence of an acid or base catalyst. The presence of unsaturated groups in the side chains of compounds present in CNSL means that polymerisation can also take place under acidic conditions without any other reactants being added.

CNSL, once polymerised with acids to a solid form, is crushed and used for many purposes, e.g. in the manufacture of clutch facings and linings. CNSL is not water-soluble and is not easily dispersed in water. The reaction of CNSL with aldehydes in the presence of sodium hydroxide gives at the earliest stages of the reaction a viscous mix which is not easily handled and makes it very difficult to make large scale use of alkali catalysed resins made from CNSL.

It would be more commercially advantageous if CNSL could be converted to a form where it can be more easily dispersed in water, and made either wholly or partially water-soluble.

SUMMARY OF THE INVENTION

We have now found that by treating CNSL with ozone and reducing the products (e.g. ozonides) so obtained, the pentadecyl chains present in the phenolic components of CNSL are converted to compounds with an eight carbon chain, the terminal group of which is an aldehyde (CHO) group. In the case of technical CNSL, some or all of any polymerised material present will be converted to the compounds with an eight carbon chain and a terminal aldehyde group. This treatment will also result in the formation of alkyl aldehydes which can be used, but are not necessary, as additional crosslinking agents. In this form CNSL can be used for the formation of composites where ready dispersibility or solubility in water of the precursor for the binder material used to form the composite is an advantage.

The treatment with ozone of CNSL has not previously been described, but it is known to use ozonolysis and reduction of the ozonides so formed to convert anacardic acid and cardanol isolated from *Gingko biloba L.* into aldehydes (Chem. Pharm. Bull. 35(7) 3016–3020). However, this was in connection with the examination of long chain phenols such as anacardic acid and cardanol for use as anti-tumour agents, and not the formation of resins for use in composites.

It is also known to use ozonolysis to form aldehyde mixtures from soya oils, see E. H. Pryde et al., The Journal of the American Oil Chemists' Society, page 376, Vol. 38, 1961. Pryde et al disclose that the aldehyde mixtures formed from the ozonolysis are used to form resins with phenol.

However, in neither of the aforementioned documents is there any suggestion that the treatment of the mixtures of long chain phenols which occur in CNSL by ozonolysis and reduction would confer advantageous properties in connection with the use of CNSL in the formation of composites.

DETAILED DESCRIPTION OF THE INVENTION

Accordingly, in one aspect of the invention, there is provided a process for modifying CNSL comprising subjecting the CNSL to ozonolysis to form ozonolysis reaction products followed by reduction of the ozonolysis reaction products to give a mixture of phenolic components and aldehydes.

In a preferred embodiment, there is provided a process for modifying CNSL which comprises the steps of first reacting CNSL with ozone for form a mixture containing ozonolysis reaction products, and secondly treating the mixture under reducing conditions to form a further mixture containing phenolic components with an eight carbon chain having a terminal CHO group and alkyl components of varying lengths with either one or two terminal CHO groups.

The reaction of CNSL with ozone is carried out in a solvent, preferably a chlorinated solvent such as, but not limited to, dichloromethane. Other solvents which can be used include cyclohexane, methanol, chloroform and hexane. The ozone can be used at concentrations in the range 1 to 10% in oxygen, and typically in contact with CNSL until ozonlysis is complete. The end point for ozonolysis can be judged using TLC, or chemical methods such as the starch iodide test. These tests are used to check periodically for the end point of the ozonolysis, i.e. when none of the components present in the starting CNSL are present in the reaction mixture.

Reduction of the ozonolysis reaction products (e.g. ozonides) can be carried out using any of a variety of reducing conditions. Thus, reduction can be effected using a suitable metal, such as a transition metal (e.g. zinc), preferably in the presence of an acid. For example, formation of the second mixture under reducing conditions can, for example, be carried out in the presence of zinc and acetic acid. Alternatively, other methods (e.g. standard methods) of achieving reducing conditions can be used and examples of such methods include catalytic hydrogenation in the presence of a metal catalyst such as a transition metal catalyst; e.g. hydrogen may be bubbled through the reaction mixture in the presence of a catalyst such as Pd—C (catalytic palladium hydroxide on calcium carbonate). Other reducing agents that can be used include iodide (e.g. sodium, potassium, calcium etc)+acetic acid; dimethyl sulphide; thiourea; triphenyl phosphine; trimethyl phosphate and pyridine.

A further alternative, and particularly preferred, reducing agent is a reducing sugar. The reducing sugar can be for example a monosaccharide or a disaccharide, and can be an aldose or a ketose sugar.

Examples of reducing sugars are hexose monosaccharide sugars such as glucose, mannose, allose, and galactose, and disaccharides such as maltose. A presently preferred sugar is alpha-D-glucose.

According to a preferred aspect of the invention, there is provided a process for modifying CNSL, comprising the steps of first reacting CNSL with ozone to form a reaction product, and secondly treating the reaction product with a reducing sugar so as to form a mixture containing phenolic components with an 8 carbon chain having a terminal CHO group, and alkyl components with either one or two terminal CHO groups.

We prefer to use a process in which the solvent present during the treatment with ozone is, or contains an alcohol, preferably ethanol. Solvents that can be used in admixture with an alcohol include chloroform, dichloromethane, hexane, and cyclohexane. We have also found that industrial methylated spirit (IMS) can be used as the solvent during the treatment with ozone.

When a sugar is used as the reducing agent, the reductive cleavage of the ozonolysis reaction product is typically carried out by stirring an aqueous solution of a reducing sugar into the reaction mixture obtained by the ozone treatment. The mixture can then be heated to a temperature where reduction takes place at a satisfactory rate to ensure a good yield of aldehyde. The temperature used is conveniently between 50° and 60° C. and a time of about two hours is usually sufficient. The product may then be purified to remove substantially all the reacted and any unreacted sugar (if any is present). We prefer, where the product is to be used in a curable composition, to simply remove solvent and use the aldehyde product in admixture with the oxidised sugar and any unreacted sugar remaining. We further prefer to use excess sugar so that unreacted sugar is present as we believe, without wishing to be bound by any theory, that the sugar may be of value in stabilising the aldehyde product in storage.

The product of the treatment of the ozonolysis reaction products under reducing conditions is, as described above, a mixture of phenolic and alkyl aldehydes. The alkyl aldehydes formed include butanal and heptanal. It is possible, but not essential, to separate the phenolic aldehydes from the alkyl aldehydes before use. Both the mixture of phenolic aldehydes left after removal of the alkyl aldehydes and the mixture in which both alkyl and phenolic aldehydes are present are hereinafter referred to as CNSL aldehydes.

In a further aspect, the invention provides a mixture of alkyl aldehydes as hereinbefore defined produced by the treatment of CNSL. Such mixtures of alkyl aldehydes are of value for uses including as crosslinking agents.

CNSL aldehydes can be converted using either acid or base catalysis into systems which on heating polymerise. We have found that the addition of an acid, particularly a sulphonic acid such a p-toluene sulphonic acid, followed by treatment with a base, results in a system which is either very finely dispersed in water, or wholly, or partially water soluble. This can also be achieved by the addition of a base, added either in an aqueous solution, or by the sequential addition of a base and water. No residue can be detected when the CNSL aldehyde aqueous material is filtered through Whatman No. 1 filter paper and a glass wool column. The CNSL aldehydes can also be used alone in the treatment of materials in particulate and/or fibrous form such as wood, straw, hemp, jute, flax, rice straw and maize, usually to form composites from these materials.

Our invention therefore also includes a method of converting CNSL aldehydes to an adhesive with an acidic material in the presence of water to form an emulsion, which on further treatment with a base is converted to a material in which only an aqueous phase is detectable.

Our invention also includes an adhesive produced by the treatment of CNSL aldehydes with an acidic material.

A further form of our invention is an adhesive formed by the treatment of CNSL aldehydes with a base.

The base can be added as an aqueous solution or by sequential addition of a base and water.

Yet another form of our invention comprises an adhesive formed by sequential addition of an acid and a base to CNSL aldehydes. In one form of this aspect of our invention, p-toluene sulphonic acid is first added to CNSL aldehydes, followed by a solution of sodium hydroxide.

Our invention also includes a method of forming composites from organic and inorganic particulate and fibrous materials comprising treating the material with CNSL aldehydes and then heating to form a composite. Pressure can be applied while forming the composite.

Examples of composites are materials formed from particulate and/or fibrous materials which can be organic or inorganic. Examples of organic materials are lignocellulosic materials such as wood, straw, hemp, jute, flax, rice straw and maize. Examples of inorganic materials include inorganic particulates and fibres, particular examples being charcoal, marble (e.g. crushed marble), crushed rock, clay, coal, slate and glass, e.g. fibre glass.

The adhesives according to our invention are of particular value in forming binders for use in the manufacture of wood particle boards. The measured properties of test wood particle boards in which the binder used has been derived from the CNSL aldehydes of the present invention exceeds that required for boards to be of a standard acceptable in the marketplace. They all exceed the European Standards for Internal Bond Strength, Thickness Swell, and Bending Strength (Standards EN 319, EN 317, and EN 310).

Our invention also includes wood particle boards whenever made using adhesives formed from CNSL aldehydes.

The acids used in the formation of the adhesives from CNSL aldehydes include mineral acids such as sulphuric acid and phosphoric acid, and sulphonic acids such as p-toluene sulphonic acid.

The base used is usually sodium hydroxide in aqueous solution, but other bases such as potassium hydroxide, ammonia and amines can be used. Sodium hydroxide is conveniently used as a 30% solution in water.

The following examples illustrate but do not limit the invention.

EXAMPLE 1

CNSL (3.2 g, ~10 mmol) was added to dichloromethane (10 ml) and the dispersion formed then cooled to −78° C. in a bath of dry ice and acetone. Ozone is passed into the CNSL dispersion at about 52 mmol/hour until the reaction is completed. This takes about two and a half hours. The completion of ozonization is judged by Thin Layer Chromatography (silica gel eluted by 20%/80% (v/v) ether/ petroleum ether (b.p. 40°–60° C.). Zinc (5 g) and glacial acetic acid (10 ml) are added to the ozonised CNSL and the mixture is warmed rapidly to room temperature, 20° C., in a water bath, and stirred at that temperature for two hours, after which the zinc is filtered off and dichloromethane is removed by evaporation in a rotary evaporator under reduced pressure. The presence of a mixture of CNSL aldehydes was confirmed by infrared and NMR spectroscopy and HPLC.

If desired, but not necessarily, the alkyl aldehyde compounds, which are water soluble, in the CNSL aldehyde mixture can be separated from the CNSL phenolic aldehydes by extracting the filtrate with a mixture of water and ether, in which case the CNSL phenolic aldehydes form a solution in ether. In this example the CNSL aldehydes were separated in this way. The ether was removed by rotary evaporation. The phenolic CNSL aldehydes were used to form an adhesive: thus 4 g of the CNSL phenolic aldehyde mixture was mixed with 0.8 g of para-toluene sulphonic acid and 0.8 g of 30% NaOH solution in water was added. An acid solution consisting of 0.5 g of para-toluene sulphonic acid, 0.5 g 98% sulphuric acid and 3 g of water was then added. A non-viscous adhesive composition apparently containing only one phase was obtained by adding 8 g of 30% NaOH solution in water. It was found that this adhesive could be readily polymerised by heating at a temperature chosen from the range 90° C. to 180° C.

EXAMPLE 2

160 g of CNSL was diluted with 750 ml of dichloromethane in a flask fitted with a high powered overhead mechanical stirrer. The flask was placed in a dry ice/acetone bath and cooled to −78° C. with the stirrer operating. Once the mixture had been cooled, addition of ozone commenced from a generator with a capacity of 8 g per hour. Ozonisation was monitored using TLC, and the end point of ozonolysis judged by the absence of the components present in the mixture at the start of the reaction with ozone.

200 g zinc dust was then added, followed by the slow addition of 500 ml glacial acetic acid, the mixture was vigorously stirred during the addition of the acetic acid, to prevent freezing of the acetic acid. The reaction mixture was left in the dry ice/acetone bath and allowed to warm up slowly to ambient temperature with water being added to the bath. Stirring was continued overnight, and then any remaining zinc dust was filtered off using vacuum. CNSL phenolic aldehydes were extracted, as in Example 1, from the CNSL aldehyde mixture, and 5 g of the CNSL phenolic aldehyde mixture were placed in a beaker. 1 g of para toluene sulphonic acid was added while stirring with a glass rod, followed by 1 g of NaOH and then 5 g of a 12.5% (v/v) aqueous solution of para toluene sulphonic acid. The slow addition of 10 g of 30% NaOH as a solution in water, with stirring, produced an apparently single phase adhesive. It was found that this adhesive could be readily polymerised by heating at a temperature chosen from the range 90° C. to 180° C.

EXAMPLE 3

CNSL (128 g ~0.4 mol) was added to dichloromethane (1 liter) and the solution thus formed cooled to −78° C. in a bath of dry ice and acetone. Ozone was passed into the solution at about 0.17 mol/hour (8 g/hour) until the reaction was completed. This was monitored, as in Example 2, using Thin Layer Chromatography, and the end point of the reaction was reached after about three hours. Zinc (160 g) and glacial acetic acid (400 ml) were added to the ozonised CNSL, and the mixture warmed very slowly to room temperature with vigorous stirring. Stirring was continued for two hours after which the zinc was filtered off and dichloromethane was removed by evaporation in a rotary evaporator under reduced pressure. CNSL phenolic aldehydes were extracted, as in Example 1, from the CNSL aldehyde mixture, and their structure confirmed by infrared and NMR spectroscopy, and analysis by HPLC.

The CNSL phenolic aldehydes were then used to produce both an alkali catalysed adhesive, and an acid catalysed adhesive as described below.

Alkali Catalysed (a) CNSL phenolic aldehyde (275 g) was placed in a two-liter flask fitted with an overhead mechanical stirrer and 55 g of solid p-toluene sulphonic acid was added while stirring. 55 g of 30% NaOH solution in water was added followed by 275 g of 12.5% (v/v) aqueous solution of p-toluene sulphonic acid. The further slow addition with stirring of 275 g of 30% NaOH solution in water produced an adhesive which could be readily polymerised by heating at a temperature chosen from the range 90°–180° C.

(b) 0.5 g (2.27 mmol) CNSL phenolic aldehyde was placed in a beaker and 0.65 g (2.27 mmol) of 13.6% NaOH solution in water was added slowly, while stirring with a glass rod. A thin paste formed, to which 0.3 g of deionised water was added, followed by the addition of 0.3 g (1.03 mmol) of 13.6% NaOH. An adhesive was formed which was polymerisable by heating.

Acid Catalysed 60 g of CNSL phenolic aldehyde was mixed with 12 g of solid p-toluene sulphonic acid and 24 gm of water added, which formed a paste when stirred vigorously with a glass rod. The adhesive thus formed had a shelf life of about 40 minutes.

Use of Adhesive in Particleboard

Test particle boards were formed using both the alkali and acid catalysed adhesives. Particle board is formed by pressing a wood particle/adhesive mixture in a die with a preheated punch to e.g. 6 mm stops at an elevated temperature for several minutes. It is necessary to ensure that at its core the material being pressed reaches a high enough temperature for a sufficient time to cure the adhesive. The final dimensions of the product depending on the shape of the die and the pressure applied.

The experimental boards were made from wood chips sieved to remove fines below 1 mm and particles greater than 5 mm. The wood had a moisture content of 5.8% (w/w dry wood). Sufficient adhesive was mixed with the wood particles to give a solids content of 14% w/w based on dry wood content. The boards were pressed in a die to give boards with a density of 750 g/m$^3$, a diameter of 312 mm and a thickness of 6 mm. Pressing in the die was carried on for ten minutes at a temperature of 140° C. The boards on testing all exceeded the European Standards for Internal Bond Strength, Thickness Swell and Bending Strength (EN 319, EN 317, and EN 310) thus demonstrating that binders formed by curing the adhesives of the present invention are of commercial value, and that CNSL can be used as a source of easily used adhesives.

Examples 1 and 2 describe the ozonolysis of CNSL and subsequent reductive cleavage of the ozonolysis reaction products using zinc and acetic acid. The following examples illustrate the use of sugars as the reducing agents.

EXAMPLE 4

500 g of CNSL is dissolved in 2.5 liters of IMS and placed in a 5 liter flask fitted with an overhead stirrer. Ozone in oxygen is bubbled through the solution at a rate of 10 liters per minute until no starting material can be detected by Thin Layer Chromatography (TLC) (silica gel plate developed in 20:80 ether petroleum spirit). 300 g of alpha-D-glucose is dissolved in 500 ml of water and added to the reaction vessel. The contents of the vessel are heated to 50° C. for 2 hours and left over night at 25° C. The IMS is removed under reduced pressure. On standing the mixture separates into an oily layer containing the aldehyde product and a water layer. The oily layer will contain unreacted sugar and oxidised sugar formed during the reduction. The oily layer may be used to form adhesives and composites in the manner described above in Examples 1 and 2.

EXAMPLE 5

The procedure described in Example 1 was repeated with an additional purification step where the oily layer was subject to repeated extraction with a 1:1 ether/water mixture until a clear solution was observed in the aqueous phase. The ether was removed from the ethereal phase leaving 473 g of 8-(3-hydroxy-phenyl)-octanal which could be used as an adhesive in the formation of composites as described above.

It will readily be apparent that numerous modifications and alterations can be made to the processes described in the foregoing examples without departing from the principles underlying the invention, and all such modifications and alterations are intended to be embraced by this application.

We claim:

1. A composite comprising at least one of a particulate or a fibrous material, and a resin, wherein the resin is obtained from the ozonolysis of CNSL to form ozonolysis reaction products, followed by the reduction of the reaction products to form a mixture of phenolic components and aldehydes.

2. A composite according to claim 1, wherein the phenolic components comprise an eight carbon chain having a terminal —CHO group and wherein the aldehydes comprise alkyl components of varying lengths having at least one terminal —CHO group.

3. A composite according to claim 1, wherein the ozonolysis reaction products are reduced according to one of the methods in the group consisting of reduction with metals in the presence of acid, reduction using sugars, reduction of catalytic hydrogenation, and reduction using an agent chosen from the group consisting of iodide compounds in the presence of acetic acid, dimethyl sulfide, thiourea, triphenyl phosphine, trimethyl phosphate and pyridine.

4. A composite according to claim 3, wherein the reducing agent is zinc in the presence of acetic acid.

5. A composite according to claim 3, wherein the reducing agent is a sugar and is alpha D-glucose.

6. A composite according to claim 1, wherein the ozonolysis reaction products are treated with a reducing sugar to form a mixture comprising phenolic components with an eight carbon chain having a terminal —CHO group, and alkyl components with at least one terminal —CHO group.

7. A composite according to claim 1, wherein the ozonolysis of CNSL is carried out in an alcohol solvent.

8. A composite according to claim 7, wherein the solvent is ethanol.

9. A composite according to claim 1, wherein the phenolic components and aldehydes are separated.

10. A composite according to claim 1, which is a wood particle board.

11. A composite comprising at least one of a particulate or a fibrous material, and an adhesive, wherein the adhesive is obtained from the ozonolysis of CNSL to form ozonolysis reaction products, followed by the reduction of the reaction products to form a mixture of phenolic components and aldehydes, followed by the separation of the phenolic components and the aldehydes, and then treating the aldehydes with one or both of an acidic material or a base.

12. A composite according to claim 11, wherein the adhesive is formed by sequential addition of an acid and a base to the aldehydes.

13. A composite according to claim 11, wherein the adhesive is formed by the sequential addition of p-toluene sulfonic acid and a solution of sodium hydroxide to the aldehydes.

14. A composite according to claim 11, which is a wood particle board.

* * * * *